United States Patent
White et al.

(10) Patent No.: US 9,271,854 B2
(45) Date of Patent: Mar. 1, 2016

(54) COLLAPSING STRUCTURE FOR REDUCING THE DIAMETER OF A STENT END

(75) Inventors: Sharon White, Wexford (IE); Michael Ryan, Limerick (IE); Vincent McHugo, Tipperary (IE); John Neilan, Galway (IE); Margaret Long, Limerick (IE)

(73) Assignee: Cook Medical Technologies LLC, Bloomington, IL (US)

( * ) Notice: Subject to any disclaimer, the term of this patent is extended or adjusted under 35 U.S.C. 154(b) by 871 days.

(21) Appl. No.: 13/016,421

(22) Filed: Jan. 28, 2011

(65) Prior Publication Data

US 2012/0041538 A1  Feb. 16, 2012

Related U.S. Application Data

(60) Provisional application No. 61/299,864, filed on Jan. 29, 2010.

(51) Int. Cl.
  *A61F 2/06* (2013.01)
  *A61F 2/88* (2006.01)
  *A61F 2/90* (2013.01)
  *A61F 2/95* (2013.01)

(52) U.S. Cl.
  CPC . *A61F 2/885* (2013.01); *A61F 2/90* (2013.01); *A61F 2002/9528* (2013.01); *A61F 2230/005* (2013.01); *A61F 2230/0013* (2013.01); *A61F 2230/0071* (2013.01)

(58) Field of Classification Search
  CPC ............... A61F 2002/9511; A61F 2002/9528; A61F 2002/9534; A61F 2/95; A61F 2/86; A61F 2/90
  USPC ..................... 623/1.11, 1.12, 1.23
  See application file for complete search history.

(56) References Cited

U.S. PATENT DOCUMENTS

| | | | |
|---|---|---|---|
| 4,913,141 A * | 4/1990 | Hillstead | 623/1.11 |
| 6,821,291 B2 | 11/2004 | Bolea et al. | |
| 7,252,680 B2 | 8/2007 | Freitag | |
| 2006/0190075 A1 | 8/2006 | Jordan et al. | |
| 2006/0276887 A1* | 12/2006 | Brady et al. | 623/1.53 |

(Continued)

FOREIGN PATENT DOCUMENTS

| | | |
|---|---|---|
| DE | 10 2008 01473 | 9/2008 |
| EP | 1 518 518 | 3/2005 |
| EP | 1 870 057 | 12/2007 |

(Continued)

OTHER PUBLICATIONS

Notification of Transmittal of the International Search Report and the Written Opinion of the International Searching Authority, or the Declaration issued Apr. 28, 2011 in Appln. No. PCT/US2011/022987 (10 pgs).

*Primary Examiner* — Katherine Rodjom
(74) *Attorney, Agent, or Firm* — Brinks Gilson & Lione

(57) ABSTRACT

A collapsing structure for collapsing the crowns of a stent and method of use thereof are described. The collapsing structure comprises an inner filament engaged to an outer filament. The outer filament is interwoven through at least a portion of the crowns of the stent end so as to create a plurality of loops. The inner filament is interwoven through at least a portion of the loops of the outer filament. Pulling on the inner filament causes the loops of the outer filament to be pulled radially inward, thereby pulling the crowns towards each other to collapse the stent end.

24 Claims, 14 Drawing Sheets

(56) References Cited

U.S. PATENT DOCUMENTS

2009/0182407 A1* 7/2009 Leanna et al. ............... 623/1.11
2010/0010517 A1* 1/2010 Stopek .................. A61B 17/11
　　　　　　　　　　　　　　　　　　　　　　606/153

FOREIGN PATENT DOCUMENTS

| | | |
|---|---|---|
| JP | 2008-514370 A | 5/2008 |
| WO | WO 2006/037086 A1 | 4/2006 |
| WO | WO 2006/124541 | 11/2006 |

* cited by examiner

US 9,271,854 B2

COLLAPSING STRUCTURE FOR REDUCING THE DIAMETER OF A STENT END

This application claims priority to U.S. Provisional Application Ser. No. 61/299,864, filed Jan. 29, 2010.

BACKGROUND

Stents are being used increasingly in benign indications. Such use requires the ability to remove the stent when its use has become redundant. Additionally, misplacement of the stent may be a risk during stent deployment. For example, foreshortening braided stents can be deployed at an incorrect target site within a body lumen. The ability to reposition the stent within the body lumen or remove the stent from the body lumen after deployment with minimal trauma to the patient would be advantageous. Although the inventions described below may be useful for repositioning or removing a deployed stent, the claimed inventions may also solve other problems.

SUMMARY

Accordingly, a collapsing structure is provided comprising an outer filament interwoven with a stent end and an inner filament interwoven with the outer filament at one or more engagement points thereof, wherein the stent end is collapsed by drawing the inner filament together.

The invention may include any of the following aspects in various combinations, and may also include any other aspect described below in the written description or in the attached drawings.

In a first aspect, a collapsing element for removing or repositioning a stent is provided. The collapsing element comprises a first filament and a second filament. The first filament is interwoven through a plurality of crowns extending about a stent end. The interweaving of the first filament through the plurality of crowns creates a plurality of loops disposed about the stent end. The second filament is interwoven through two or more of the plurality of the loops of the first filament. The second filament is configured to be pulled so as to pull the loops of the first filament radially inwards and thereby pull the plurality of crowns towards each other to collapse the stent end.

In a second aspect, a collapsing structure is provided. The system comprises an outer filament interwoven through a plurality of crowns about a stent end to create an alternating arrangement of a plurality of inner loops and a plurality of outer loops. The plurality of inner loops is disposed within a lumen of the stent and the plurality of outer loops is disposed outside an exterior surface of the stent end. An inner filament is interwoven through each of the plurality of the inner loops to create a plurality of engagement points for pulling the outer filament. Pulling the outer filament at each of the plurality of engagement points draws the plurality of crowns inwardly toward a central longitudinal axis of the stent.

In a third aspect, a device for collapsing an end of a stent is provided. A two-filament system comprising an outer filament interwoven through at least a portion of a plurality of crowns along the stent end to create a plurality of loops is provided. The system also includes an inner filament passing through the outer filament to create a plurality of engagement points therebetween. As the inner filament is pulled at each of the plurality of engagement points, the outer filament is tightened against the plurality of crowns. The crowns of the stent end are thereby pulled radially inward so as to collapse the stent end.

BRIEF DESCRIPTION OF THE DRAWINGS

Embodiments will now be described by way of example with reference to the accompanying drawings, in which.

DETAILED DESCRIPTION OF THE EMBODIMENTS

Figure 1:
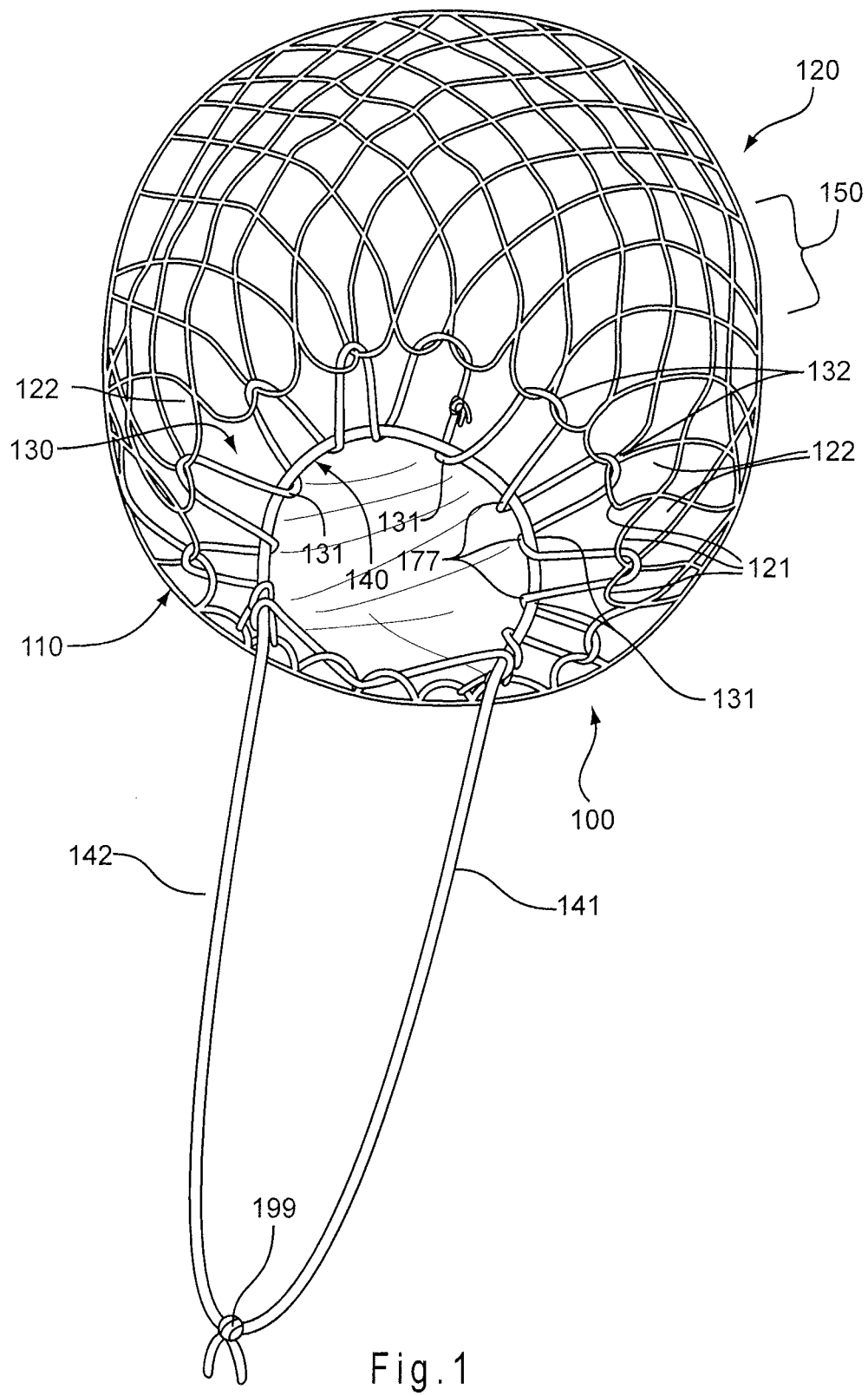
FIG. 1 shows the end of a stent in a slightly compressed state and having an outer filament interwoven through all of the crowns of the stent end and an inner filament extending through the loops of the outer filament.

The embodiments are described with reference to the drawings in which like elements are referred to by like numerals. The relationship and functioning of the various elements of the embodiments are better understood by the following detailed description. However, the embodiments as described below are by way of example only, and the invention is not limited to the embodiments illustrated in the drawings. It should also be understood that the drawings are not to scale and in certain instances details have been omitted, which are not necessary for an understanding of the embodiments, such as conventional details of fabrication and assembly.

Throughout the specification, the terms "distal" and "distally" shall denote a position, direction, or orientation that is generally away from the physician. Accordingly, the terms "proximal" and "proximally" shall denote a position, direction, or orientation that is generally towards the physician.

The ability to collapse a stent end after the stent has been deployed in a body lumen enables the stent to be repositioned to another location within the body lumen. For example, repositioning of the stent can be advantageous when the stent has been deployed at an unintended target site, which tends to be a risk associated with stents that undergo foreshortening upon deployment. Collapsing the stent end also allows the stent to be removed from the body lumen. In one example, the ability to remove a deployed stent (e.g., a stent that is fully covered) from the body lumen after a predetermined time period can allow the stent to be used to treat benign indications that may be treatable with non-removable stents.

Referring now to the FIGS. 1-12, a collapsing structure for reducing the diameter of a stent end will be described. As will be discussed below, the collapsing structure includes an outer filament and an inner filament. The outer filament is affixed about or to the stent. In particular, the outer filament is interwoven through the crowns extending about a stent end. The inner filament is interwoven within openings of the outer filament. Generally speaking, pulling the inner filament tightens the outer filament against the outer surface of the crowns of the stent end, which causes the crowns of the stent to move radially inward, thereby collapsing the stent end. The term "filament" as used throughout the specification may include suture material, and may also include thin wire, such as nitinol. The term "crown" as used throughout the specification includes the strut of the stent forming the edge thereof.

FIG. 1 illustrates a collapsing structure 100 attached to an end 110 of a stent 120. The collapsing structure 100 includes an outer filament 130 and an inner filament 140. The inner filament 140 engages with the outer filament 130 to reduce the diameter of the stent end 110. FIG. 1 shows that the end 110 of the stent 120 is partially reduced in diameter from its fully expanded state as the inner filament 140 is pulled. Specifically, when the ends 141 and 142 of the inner filament 140 are pulled as shown in FIG. 1, portions of the outer filament 130 move radially inward. As the outer filament 130 moves radially inward, the crowns 121, which are shown as extending circumferentially about the end 110 of the stent 120, begin to bend inwards towards the central longitudinal axis of the stent 120, thereby collapsing the end 110 thereof. The inward movement of the crowns 121 also causes end portion 150 to reduce in diameter. The collapsed crowns 121 and the reduction in diameter of end portion 150 may enable the stent 120 to be repositioned within a body lumen and/or removed from a body lumen after the stent 120 has been deployed.

Figure 2:
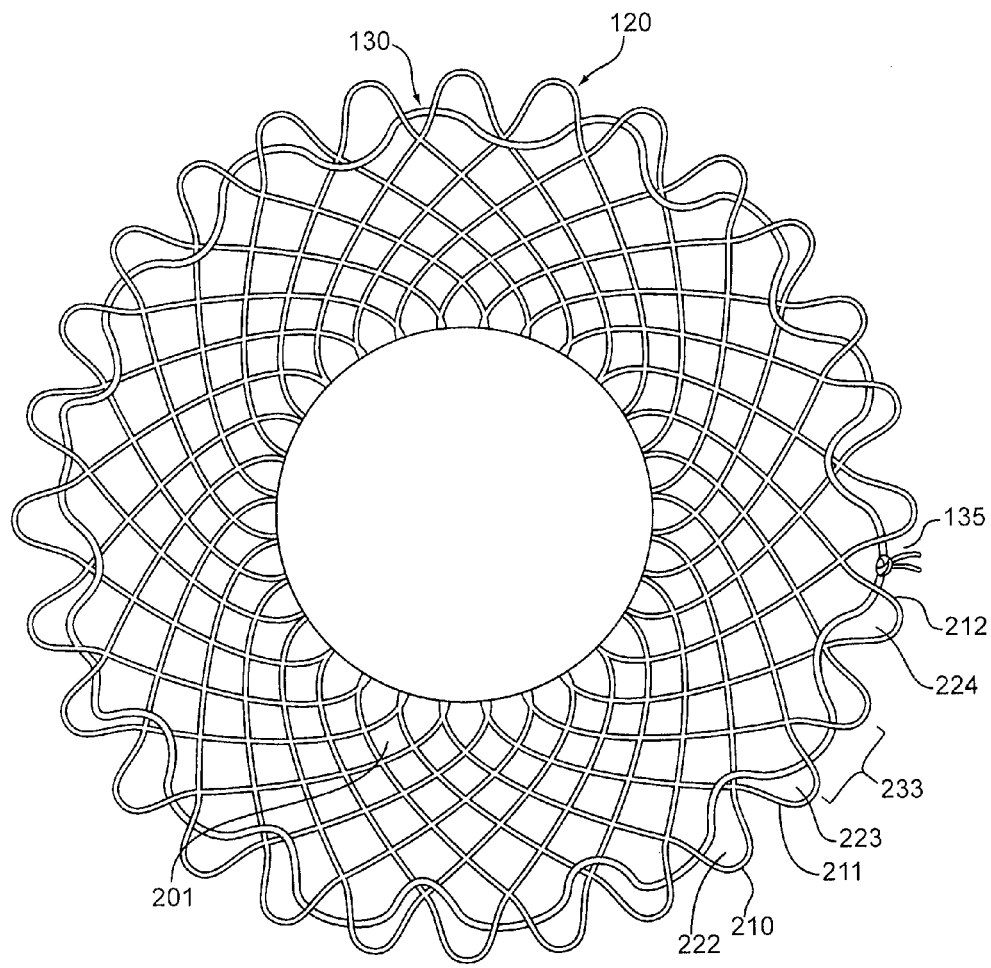
FIG. 2 is an end view of the stent of FIG. 1 in a partially expanded state and showing the outer filament interwoven through each of the crowns of the stent.

The outer filament 130 may be interwoven through the openings 122 adjacent to each of the crowns 121, as shown in FIG. 1, to create an alternating series of outer loops 132 and inner loops 131. FIGS. 1 and 2 illustrate how the outer filament 130 is interwoven through the crowns of the stent 120. The inner filament 140 has been omitted from this figure for purposes of clarity to show the pattern by which outer filament 130 interweaves about the end 110 of the stent 120. As shown in FIGS. 1 and 2, the end 110 of the stent 120 has been slightly collapsed to facilitate the process of weaving the outer filament 130 there through and to illustrate the loop pattern created by the interweaving of outer filament 130 through the crowns 121 of the stent 120. As will be explained in greater detail below, the outer filament 130 weaves through various openings 122 of the various crowns 121 residing about the end 110 of the stent 120 in an undulating pattern so as to create the series of inner loops 131 which alternate with the series of outer loops 132.

The weaving pattern for the outer filament will now be described with reference to FIG. 2, although it should be understood that other weaving patterns can be utilized. Beginning with a portion of the outer filament 130 disposed within the luminal space 201 of the stent 120, the outer filament 130 first extends outwardly through an opening 222 of crown 210. The filament 130 then emerges from within the opening 222 of the crown 210 so as to extend outside of the stent 120. The filament 130 then passes along the outside of the stent 120 as it extends away from crown 210. As the filament 130 approaches the next crown 211, the filament 130 bends inwardly towards the stent 120 and eventually passes through opening 223 of the next crown 211, which is adjacent to crown 210. The path traversed by the filament 130 between crown 210 and adjacent crown 211 creates an outer loop segment 232. After forming the outer loop segment 232, the filament 130 then passes through opening 223 of crown 211 and reemerges into the luminal space 201 of the stent 120. The filament 130 continues to travel along the crown 212 in a counterclockwise direction, as shown in FIG. 2, within the luminal space 201 of the stent 120. As the filament 130 continues to travel along the second crown 211, the filament 130 begins to bend outwardly and away from the luminal space 201 of the stent 120. When the filament 130 approaches the third crown 212, it emerges through the opening 224 thereof. The path traversed by the filament 130 between the second crown 211 and the third crown 212 creates an inner loop segment 233. The filament 130 then passes through the opening 224 of the third crown 212. The filament 130 continues to interweave into and out of each of the successive crowns in the same manner as described above so as to create a series of inner loops 131 alternating with a series of outer loops 132, as shown in FIG. 1. The free ends of the outer filament 130 may be twisted or tied to form a knot 135, as shown in FIG. 2, so as to form a continuous loop about the end 110 of the stent 120.

Figure 3:
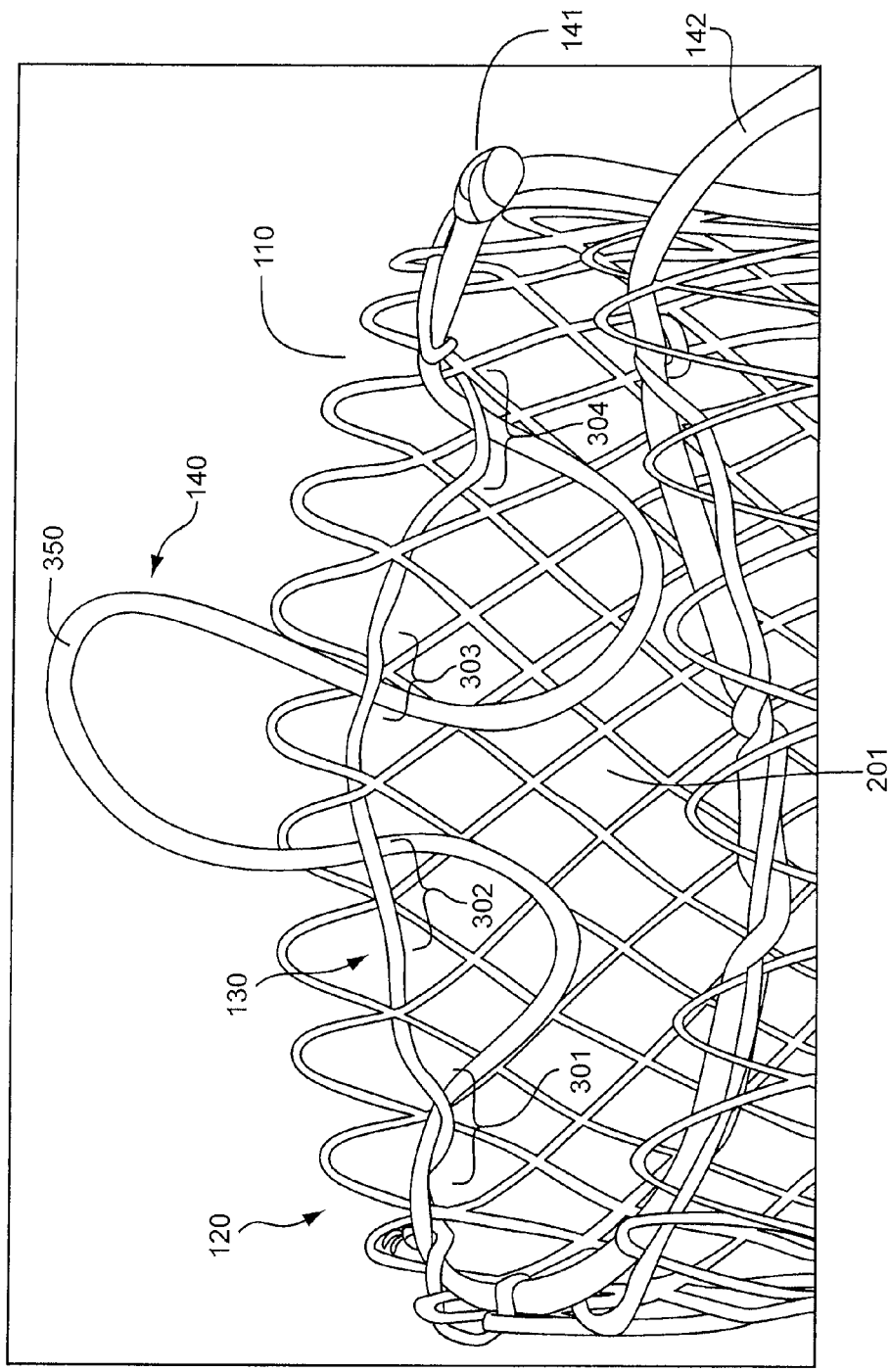
FIG. 3 shows an inner filament being interwoven through the loops created by the outer filament of FIG. 2.

Having interwoven the outer filament 130 through the crowns 121 of the stent 120, the inner filament 140 can now be interwoven through the inner loops 131 of the outer filament 130. Alternatively, and by way of example only, the inner filament 140 can be woven though the outer loops 132 of the outer filament 130. FIG. 3 shows the inner filament 140 being woven through a plurality of the inner loops 131 created by the weaving of the outer filament 130 into and out of the openings 122 of the crown 121, as described above. Unlike the weaving of the outer filament 130 within the interior and exterior of the stent 120, the inner filament 140 is only woven along the interior of the stent 120.

FIG. 3 illustrates the step of weaving inner filament 140 though the outer filament 130. Because the stent 120 is more expanded in FIG. 3 than in FIG. 2, the sizes of the inner loops 131 of the outer filament 140 appear to be smaller. However, and as will be understood by one skilled in the art, the sizes of the inner loops 131 will depend on the length of the outer filament 130, the diameter of the stent 120, and the state of collapse of the stent 120. The inner loops 131 of FIG. 1 are shown in FIG. 3 as 301, 302, 303, and 304.

Figure 3A:
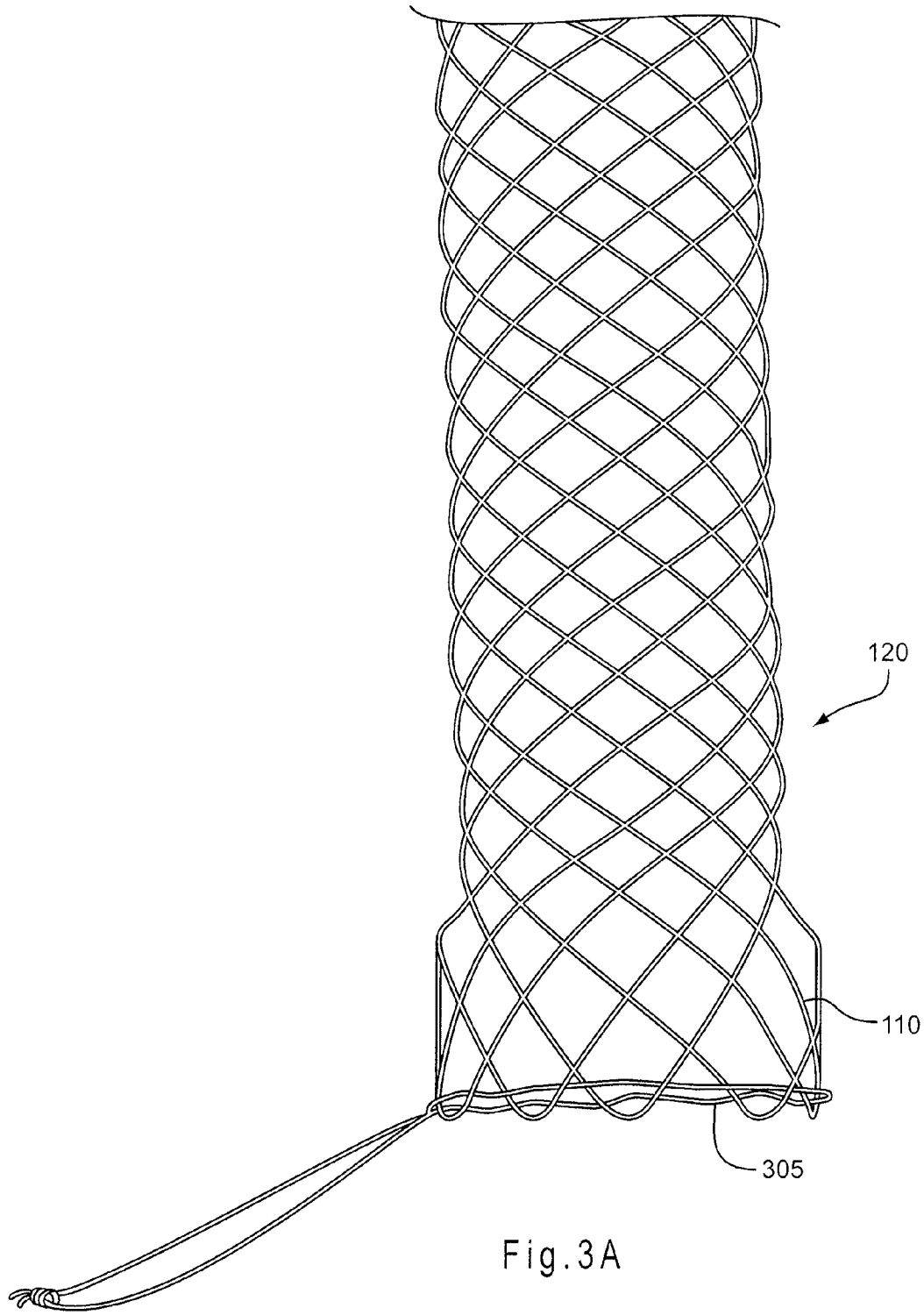
FIG. 3a shows an end view of the stent of FIG. 1 with a flared end.

For example, in certain embodiments, it may be desirable to provide an outer filament 130 having a length that is less than the circumference of the end 110 of the stent 120. In such a configuration, the outer filament 130 would cause the end 110 of the stent 120 to maintain a partially collapsed state. Similarly, it may desirable to provide an outer filament 130 having a length that is equal to the circumference of the stent 120, but interwoven through an outwardly flared end 110 of the stent 120 (i.e., the end 110 has a unrestrained diameter that is greater than that of the stent body). Such a configuration would result in a stent 120 having a uniform diameter, but having an end 110 that is more resistant to compression (i.e., has a greater outwardly directed spring constant). This configuration creates an in-built higher radial force in the end 110 that allows the stent end 110 to open quicker and recover its original diameter. The flared end 110 embodiment is illustrated in FIG. 3a, along with a single outer lasso 305, but it should be understood that a double filament structure such as that shown in FIG. 3 could be used with the flared end 110 illustrated in FIG. 3a.

Still referring to FIG. 3, inner filament 140 is woven in an undulating pattern through the first inner loop 301 within the luminal space 201 of stent 120. Having extended through the first inner loop 301, inner filament 140 is shown to then extend downwards within the luminal space of stent 120 and thereafter extend upwards through the second inner loop 302. The inner filament 140 thereafter extends upwards beyond the end 110 of stent 120 as shown at location 350 and then travels downwards towards the end 110 of the stent 120 through the third inner loop 303. Next, filament 140 loops upwards so as to extend through a fourth inner loop 304. The filament 140 may continue to propagate in this manner through each of the inner loops of the outer filament 130. FIG. 3 shows that the inner filament 140 may interweave in a substantially perpendicular orientation relative to outer filament 130. However, when the stent 120 is fully expanded, the inner filament 140 may interweave in a substantially parallel orientation relative to the outer filament 130.

After the inner filament 140 has extended through the inner loops of outer filament 130, the free ends 141 and 142 of the inner filament 140 may extend beyond the end 110 of the stent 120 (shown in FIG. 1 as extending out of the plane of the page) for a predetermined distance. The free ends 141 and 142 may be tied together to form a knot 199, as shown in FIG. 1. The knot 199 may serve as an access or engagement point to pull the inner filament 140 during operation of the collapsed structure 100.

Figure 8:
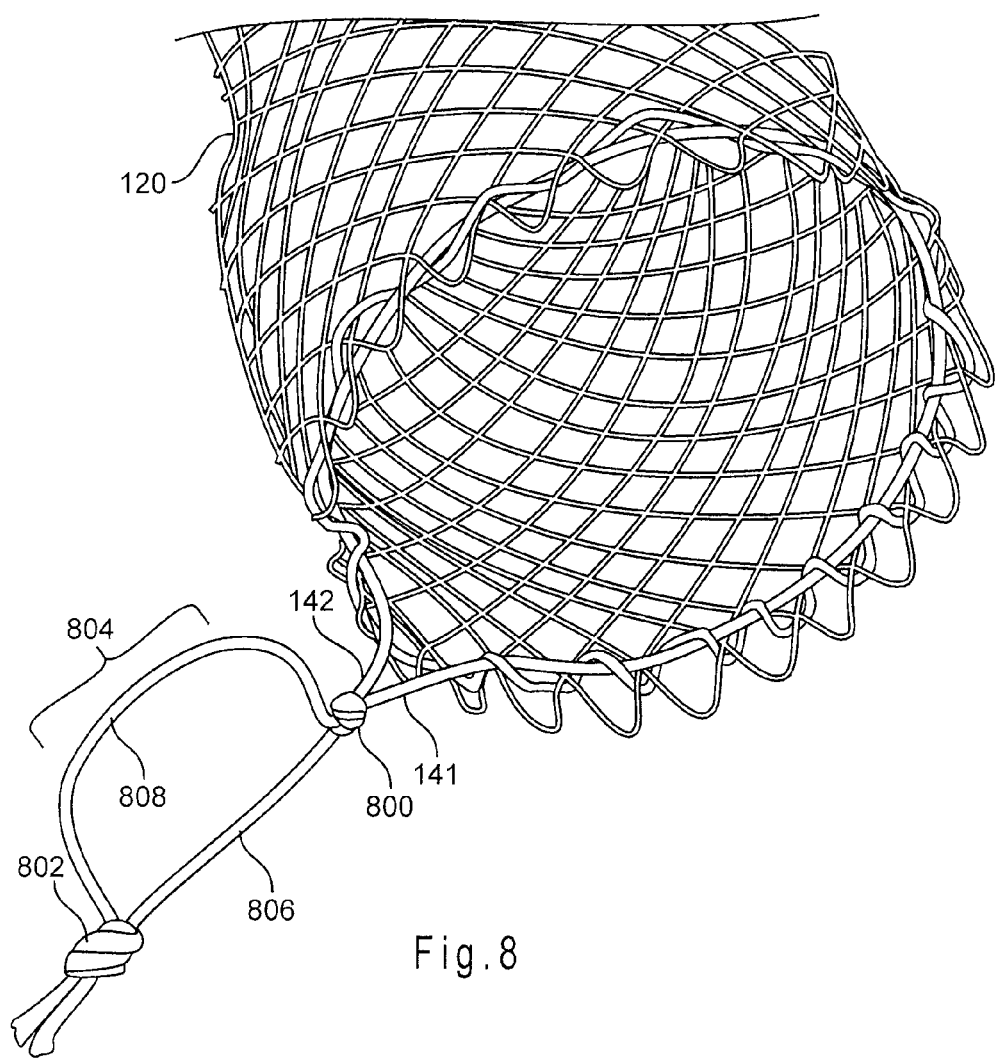
FIG. 8 shows a stent with a grasping loop structure.

Various knot arrangements may be implemented. For example, FIG. 8 illustrates a grasping loop structure. As described above, the free ends 141 and 142 may be tied together. However, as illustrated in FIG. 8, the free ends 141 and 142 are tied together to form a first knot 800 and a second knot 802, thereby forming a grasping loop 804 generally defined by a first section of suture 806 and a second section of suture 808. As shown in FIG. 8, when the free ends 141 and 142 are tied together to form the first knot 800 and the second knot 802 to form the grasping loop 804, the second section of suture 808 may be longer than the first section of suture 806, which aids the grasping loop structure in remaining open. This configuration allows easier access for removal or repositioning of the stent 120. Alternatively, the first section of suture 806 may be longer than the second section of suture 808.

Figure 8A:
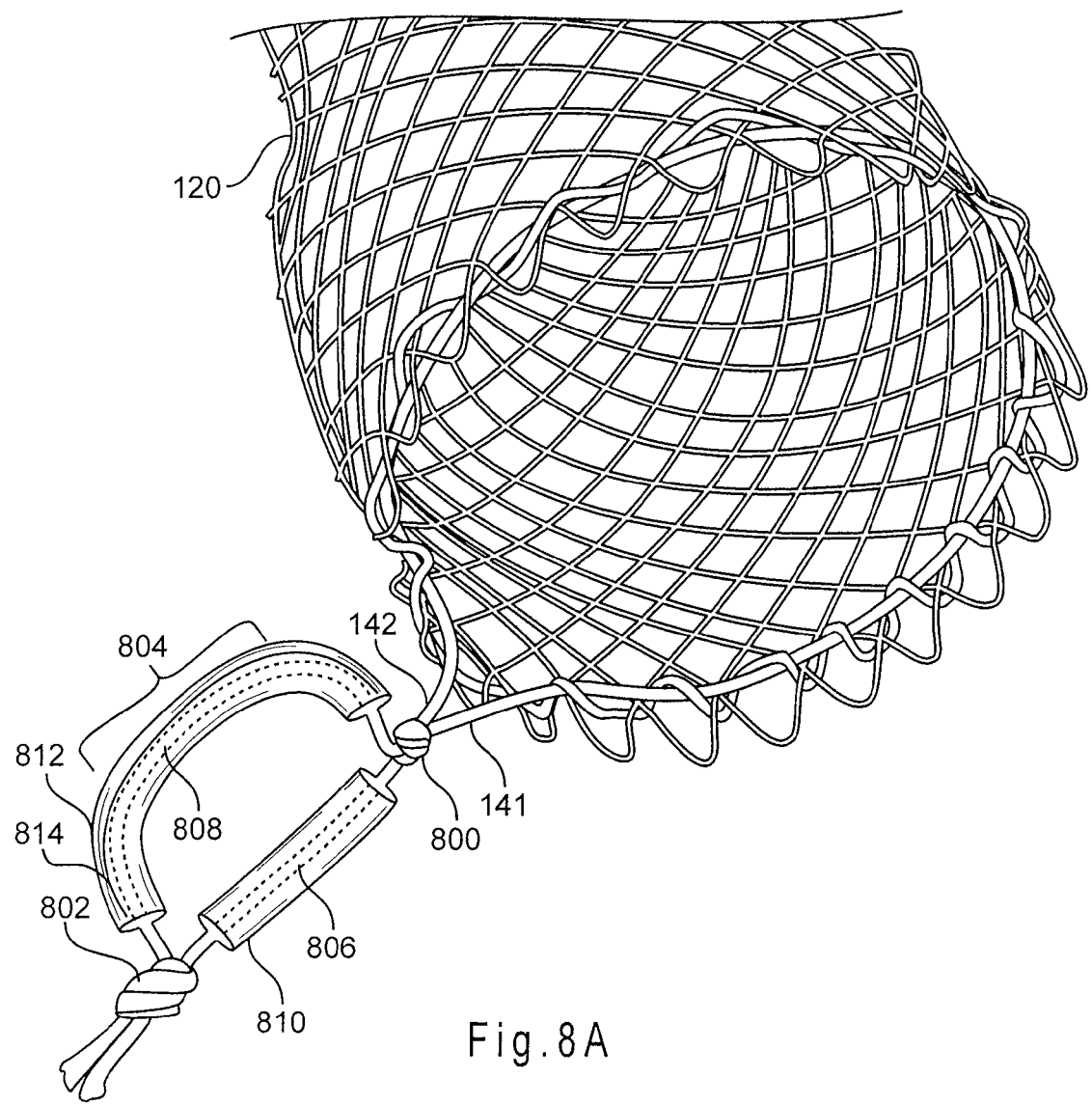
FIG. 8a shows the stent of FIG. 8 with a covering disposed on the grasping loop structure.

FIG. 8a shows the grasping loop structure of FIG. 8 with a first tube 810 disposed over the first section of suture 806 and a second tube 812 disposed over the second section of suture 808 of the grasping loop structure. Nitinol wire 814 may be included inside of the second tube 812 to aid opening of the grasping loop 804 after it has been deployed. A variety of materials may be used for the covering or tube, such as PTFE, polyurethane, polyimide, nylon, coil, polymer tubing reinforced with metal braiding, braiding, etc.

Figure 9:
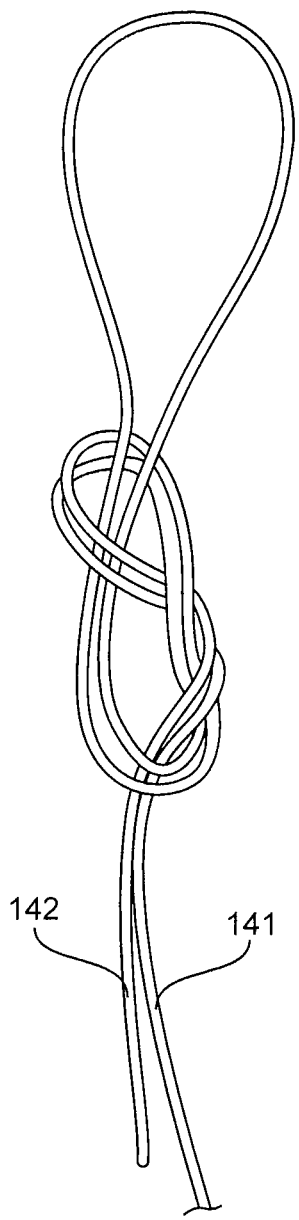
FIG. 9 shows a low-profile knot structure that may be incorporated with the stent of FIG. 1.
Figure 9A:
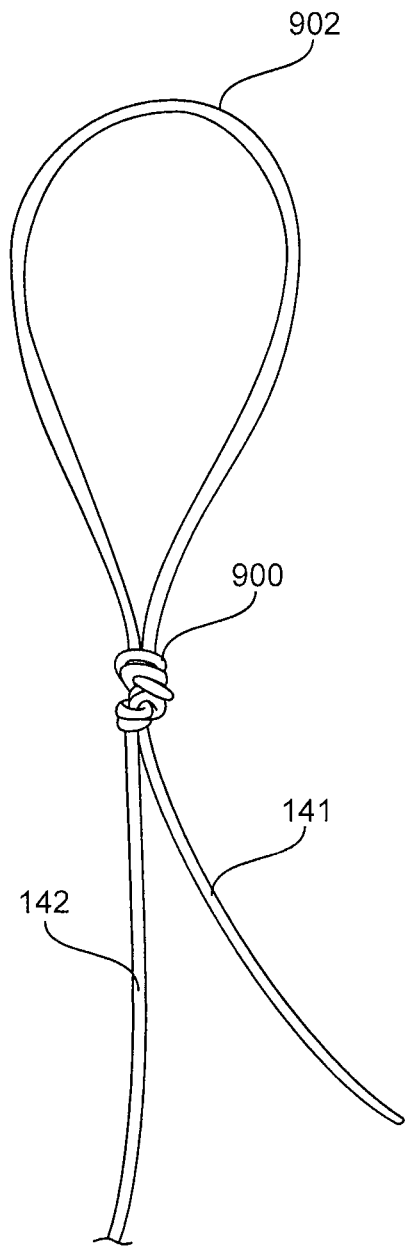
FIG. 9a shows a low-profile knot structure that may be incorporated with the stent of FIG. 1.

FIGS. 9 and 9a illustrate an alternative knot arrangement. As illustrated in FIGS. 9 and 9a, the free ends 141 and 142 are tied together to form a knot 900. Knot 900 is a low-profile knot that will not open or resist opening during use. The knot 900 forms a grasping loop 902. The low-profile of the knot 900, along with the configuration of the knot 900 and grasping loop 902, allows for removal or repositioning of the stent 120. While a certain configuration of the knot 900 is shown, any variation of a knot 900 designed to not open or resist opening during use could be implemented. For example, knot 900 could be a "double overhand knot," an "overhand knot," "figure 8 knot" or any other knot that has the characteristics to allow access for removal or reposition of the stent 120.

Figure 10:
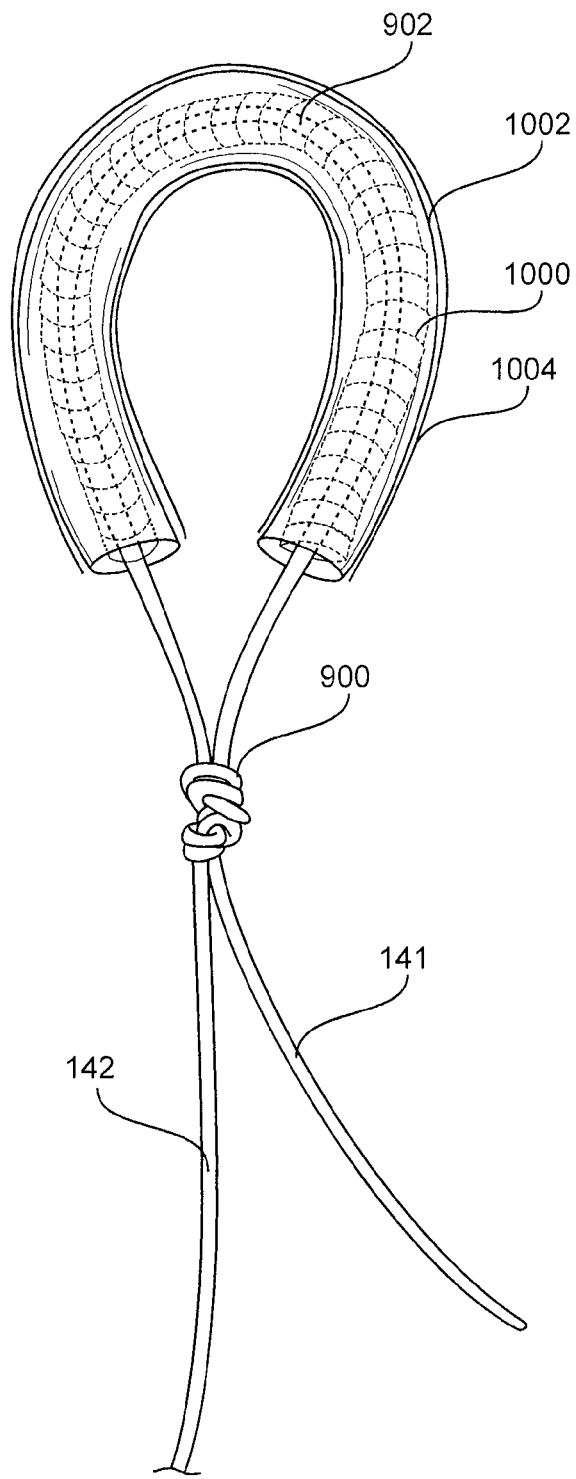
FIG. 10 shows a low-profile knot structure including a coiled wire disposed on the grasping loop structure and a covering disposed on the grasping loop structure.

FIG. 10 shows the low-profile knot structure of FIG. 9a, including a coiled wire 1000 disposed on the grasping loop 902 structure. The coiled wire 1000 may be disposed within a tube 1002, which includes a heat shrink 1004. Additionally, the coiled wire 1000 may be radiopaque coiled wire. The coiled wire 1000 allows for improved opening of the grasping loop 902 structure resulting from the spring force of the coil. The spring force of the coil may be varied depending on the coil wire implemented on the grasping loop 902, and may continuously push the grasping loop 902 into a triangular shape. The coiled wire 1000 can withstand a higher and consistent force when forceps are applied during repositioning/removal of, for example, the stent 120 (not shown). The inclusion of the coiled wire 1000 allows for retrieval of the stent 120 (not shown) post-deployment.

Figure 11:
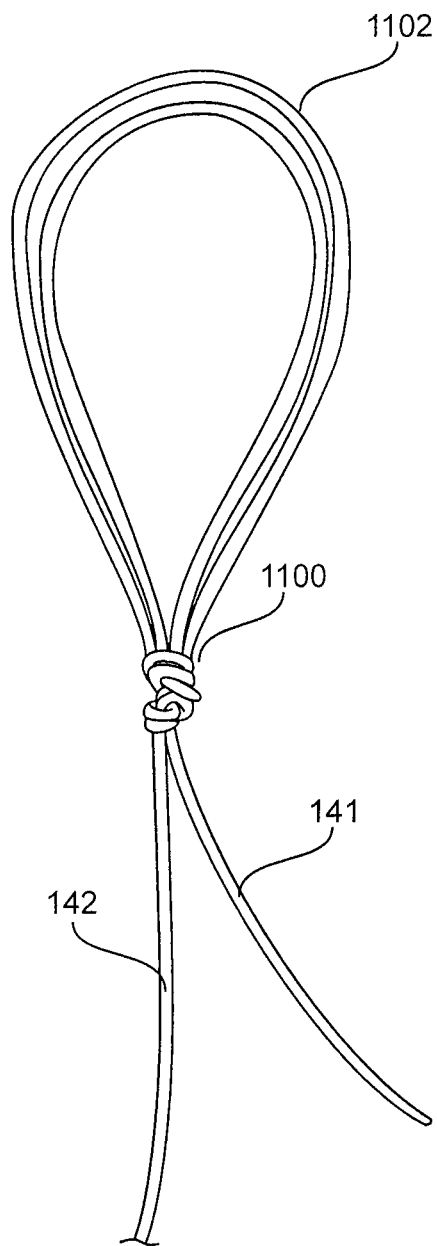
FIG. 11 shows a low-profile knot structure including a double-filament grasping loop that may be incorporated with the stent of FIG. 1.

FIG. 11 shows a low-profile knot structure including a double-filament loop 1102 that may be incorporated with the stent of FIG. 1. The free ends 141 and 142 are tied together to form a knot 1100. A double-filament loop 1102 provides additional strength for the grasping loop. The knot 1100 is a low-profile knot that resists opening during use when the grasping loop 1102 is, for example, grasped and pulled by forceps. The low-profile of the knot 1100, along with the configuration of the knot 1100 and grasping loop 1102, allows for removal or repositioning of, for example the stent 120 (not shown). While a certain configuration of the knot 1100 is shown, any variation of a knot 1100 designed to resist opening during use can implemented. For example, knot 1100 could be a "double overhand knot" or an "overhand knot." The suture used to form the knot 1100 (and the sutures disclosed herein throughout) may be made from a variety of materials such as UHMWPE (ultra-high-molecular-weight polyethylene), polyester, nylon, stainless steel, etc. However, the preferred suture material is UHMWPE because this material has very fine strands and has good resistance to cutting action of forceps.

Figure 12:
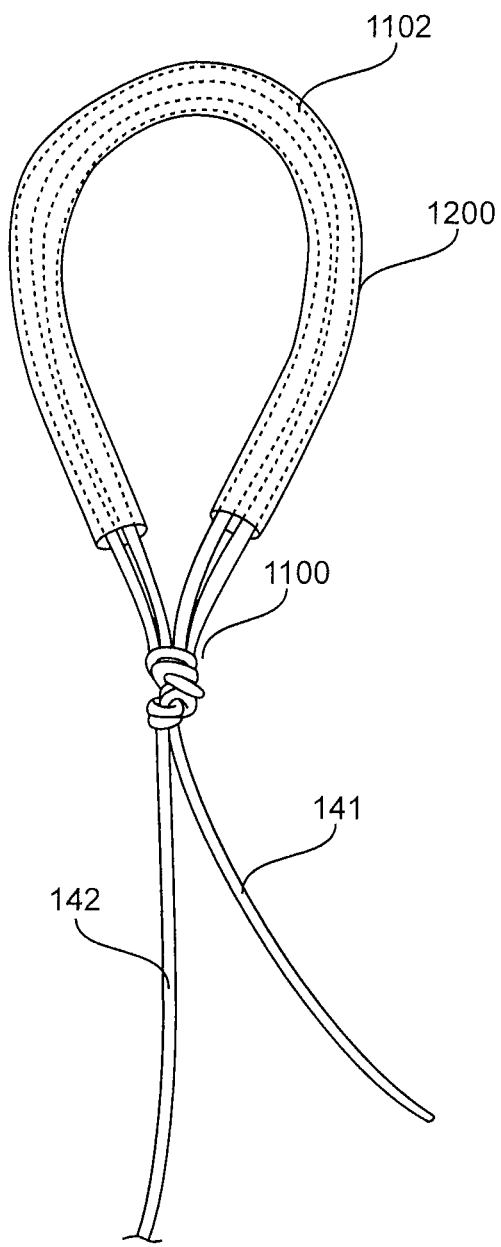
FIG. 12 shows the low-profile knot structure of FIG. 11 with a covering disposed on the double-filament loop.

The double-filament loop 1102 may be covered by a tube 1200, as shown in FIG. 12. A variety of materials may be used for the tube, such as PTFE, polyurethane, polyimide, nylon, coil, polymer tubing reinforced with metal braiding, braiding, etc. The tube 1200 provides resistance to the cutting action of forceps (not shown) by shielding the sharp edge of the forceps from the suture. The thickness of the tube 1200 is preferably greater than 0.003 inches, but the thickness may depend on the sharpness of the forceps that may be used in the removal or repositioning of the stent. The tube 1200 may be provided in a high visible color so that it is more easily seen. One method of creating the double-filament loop 1102 shown in FIG. 12 may be to thread the free ends 141 and 142 through the tube 1200, and the suture material may then be tightened to create the loop 1102 and the knot 1100. Another method of creating the double-filament loop 1102 shown in FIG. 12 may be to thread one free end through the tube 1200, then loop the free end through the tube 1200 a second time. The suture may then be tightened to create the loop 1102 and the knot 1100.

Referring back to FIG. 1, the resultant configuration of the inner filament 140 interwoven with the outer filament 130 is shown, which in turn is affixed to the end 110 of stent 120. The inner filament 140 does not itself create any loops. Rather, the inner filament 140 forms a substantially circular shape when slidably disposed through the inner loops 131 of the outer filament 130. The inner filament 140 is interwoven through the inner loops 131 with sufficient slack such that the end portion 110 of the stent 120 may fully expand following any deployment, retrieval, and/or repositioning of the stent 120. In other words, inner filament 140 is preferably not woven about outer filament 130 so tightly that the filaments 130 and 140 constrain the end 110 of stent 120, thereby preventing the end 110 from fully expanding and exerting a radial force against a body lumen. Preferably, the inner filament 140 is slidably disposed more loosely than the outer filament 130 to allow the filament 140 to be readily pulled with a grasping member (e.g., forceps). The outer filament 130 is also preferably configured to not constrain the end portions of the stent 120 when tension is released from the inner filament 140. The outer filament 130 is also free to move within the openings 122 adjacent to the crowns 121 (FIG. 1) when the end 110 of the stent 120 is partially or substantially expanded (FIGS. 2 and 3). Such movement of the outer filament 130 also enables the outer loops 132 and the inner loops 131 to change shape and/or their orientation as the crowns 121 of the stent 120 collapse in response to a pulling force applied at one or both free ends 141 and 142 of the inner filament 140. However, and as noted above, it may be desirable to limit the length or size of the outer filament if constraining or limiting the expansion of the end 110 of the stent 120 is desired.

Operation of the collapsing structure 100 will now be described. The inner filament 140 may be pulled along free ends 141 and 142 (seen in FIG. 1 as emerging out from plane of page) or at the location where the free ends 141 and 142 are tied to form a knot 199. Applying a pulling force at the free ends 141 and 142 of the inner filament 140 causes the inner filament 140 to pull at each of the apices 177 (FIG. 1) of the corresponding inner loops 131 so as to pull the inner loops 131 inwards towards the central luminal space of the stent 120. In response to the pulling force, the inner loops 131 become narrower and longer in length, the length being measured from the crowns 121 to the interior region of the apex 177 where the inner filament 140 is slidably disposed therein. As the inner filament 140 is tightened, the inner loops 131 transmit the pulling force from the inner filament 140 to the corresponding outer loops 132. In other words, the inner loops 140 pull on the outer loops 132 of the outer filament 130, thereby causing the outer loops 132 to tighten and move radially inwards. The outer loops 132 are thereby pulled radially inwards as shown in FIG. 1 against the crowns 121. FIG. 1 shows a partially collapsed configuration in which adjacent crowns 121 are pulled inwards by an outer loop 132. FIG. 1 shows that the outer loop 132 squeezes and pulls the two adjacent crowns 121 together such that the spacing between adjacent crowns 121 decreases, as compared to FIG. 3. In this manner, each of the outer loops 132 around the end 110 of stent 120 squeezes and pulls adjacent crowns 121 closer together, thereby collapsing all of the crowns 121 and also reducing the diameter of the end portion 150.

Figure 4:
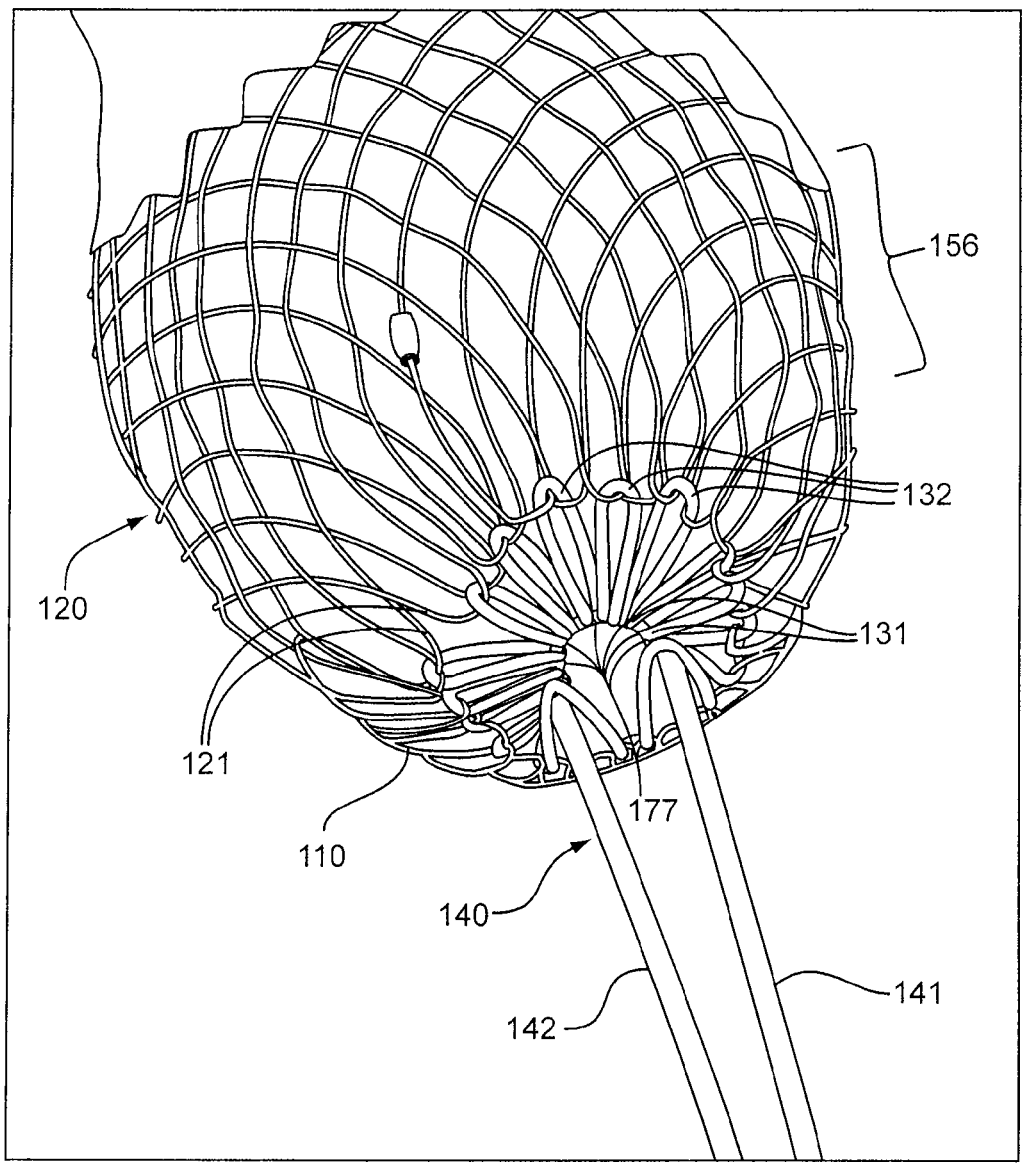
FIG. 4 shows the stent end of FIG. 3 in which the inner filament has been pulled so as to fully collapse the crowns and the stent end.

FIG. 4 shows an increased pulling force being applied at the free ends 141 and 142 of the inner filament 140 so as to completely collapse the crowns 121. FIG. 4 shows that the inner loops 131 have become narrower and longer compared to that of FIG. 1. Additionally, the outer loops 132 have become smaller in width (i.e., the width being approximately the gap between adjacent crowns 121) as they incur an increased pulling force from the inner loops 131 and the inner filament 140. The apices 177 of the inner loops 131 are shown to align about the end 110 of the stent 120 to form a substantially circular shape that is substantially concentric with the circular end 110 of stent 120. In other words, the plurality of crowns 121 as shown in their fully collapsed state in FIG. 4 substantially reside in a plane transverse to a central longitudinal axis extending through both the circular stent end 110 as defined by the crowns 121 and the shape formed by the apices 177 of the inner loops 131.

Figure 7:
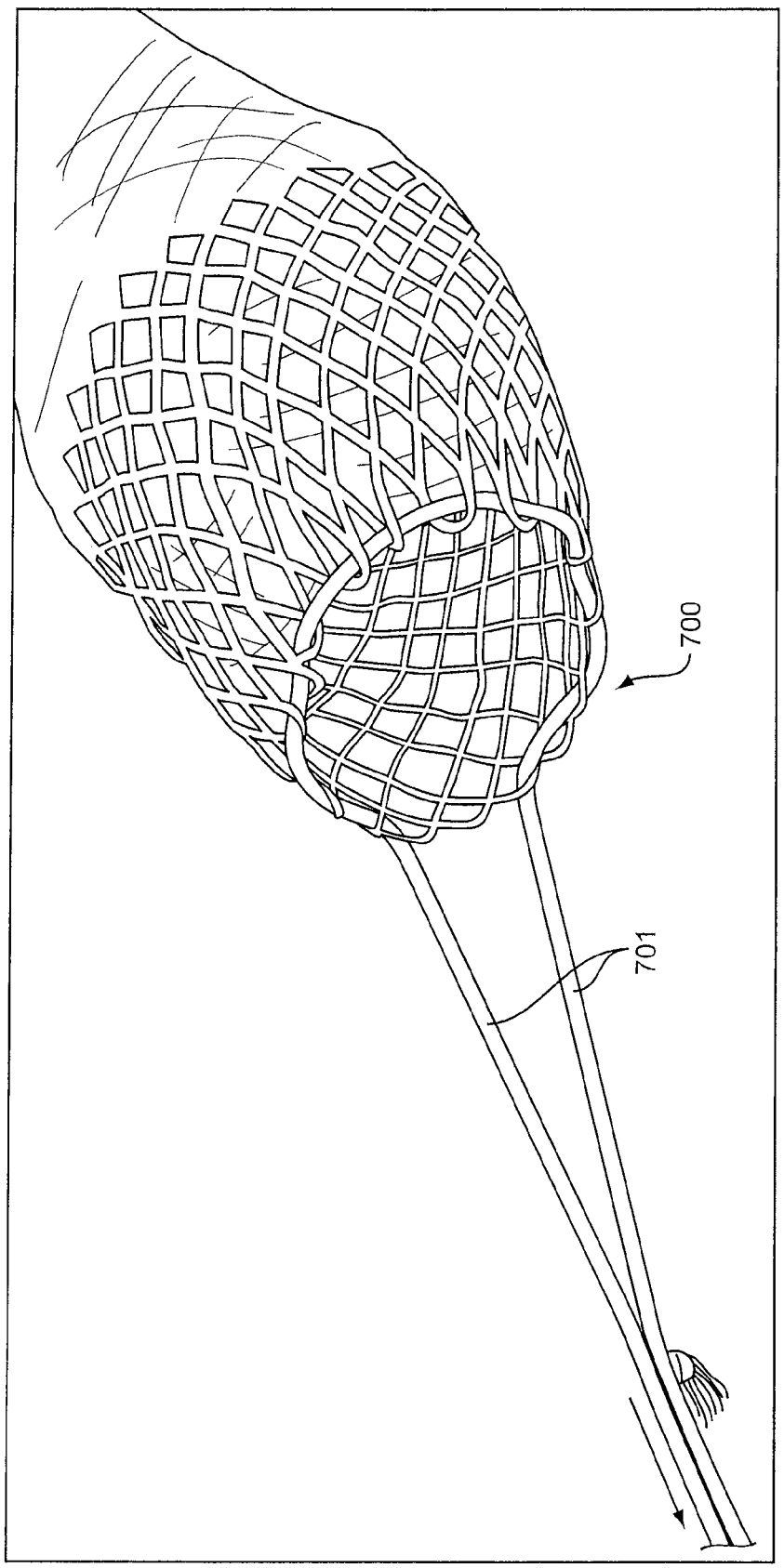
FIG. 7 shows a stent in which a single outer lasso is interwoven through all the crowns of a stent end.

The amount of force required to collapse the crowns 121 and reduce the diameter of the end portion 150 when using the above described two-filament collapsing structure 100 may be significantly less than that required when pulling directly on a single suture that is affixed to the end of a stent, as shown in FIG. 7. The lower force may be attributed in part to the significantly lower frictional resistance generated when pulling the inner filament 140 through the inner loops 131 of the outer filament 130, as compared to pulling directly on a single suture affixed to the stent end (FIG. 7). In particular, the path of the inner filament 140 through the inner loops 131 is more uniform and less undulating than the path of the outer filament 130 through the crowns 121 of the stent 120.

As mentioned above, the collapsed crowns 121 can form a substantially concentric circle with the end 110 of stent 120 shown in FIGS. 1 and 4 in which each of the crowns 121 reside in a single plane transverse to a central longitudinal axis of the stent 120. In other words, a side view of FIG. 4 would indicate that none of the crowns 121 project significantly farther in a longitudinal direction than the other crowns 121. Such an arrangement of the crowns 121 may allow the stent 120 to be pulled during repositioning within a body lumen or removal from a body lumen without significant potential of buckling and entanglement of the crowns 121. Additionally, having each of the crowns 121 reside within a single transverse plane may facilitate pushing the stent 120 out from an introducer during the deployment of stent, as all crowns 121 of the stent 120 can be pushed and released from the introducer at approximately the same time. Conversely, a non-uniform arrangement whereby some crowns are collapsed farther down than other crowns may cause only a few of the crowns which are farther collapsed to incur most of the force when pushing and releasing the stent from the introducer, which may cause some of the crowns to buckle or deform. Nevertheless, a non-uniform arrangement may have advantages for certain applications.

Entanglement of the crowns 121 may also be avoided because the two-filament collapsing structure 100 does not cause the crowns 121 to be collapsed as far as when directly pulling on a single filament affixed to a stent end (FIG. 7). As discussed above, FIG. 4 shows the fully collapsed configuration of the crowns 121. However, a separation distance or gap may remain between adjacent crowns 121, thereby preventing the crowns 121 from overlapping or criss-crossing with each other and becoming entangled. Entanglement of the crowns 121 may prevent the stent 120 from re-expanding after the stent 120 has been repositioned at a new location. Additionally, the ability of the crowns 121 to collapse radially inwards towards a central longitudinal axis of the stent 120 avoids potential trauma to the patient. Entangled crowns may inadvertently point outwards and scrape against tissue of a body wall.

It should be understood by one skilled in the art that the degree of collapse of the crowns 121 is a function of several factors, including the diameter of the stent end 110, the number of crowns 121, and the length of the outer filament 130. For example, the degree of collapse of the stent end 110 can be reduced by increasing the length of the outer filament 130, by reducing the number of crowns 121 through which the outer filament 130 is woven, or by reducing the number of inner loops 131 through which the inner filament 140 is woven.

The inner filament 140 and outer filament 130 can be formed from a variety of biocompatible materials. By way of example, the filaments 130 and 140 may be constructed of common suture material as known in the art. One type of suture material that may be used is a multifilament polyester suture commercially known as 2-0 Tevdek®. Lower frictional resistance between the inner filament 140 and the outer filament 130 can also be achieved by using various suture materials or other types of nonabrasive materials such as flexible wire. Both the inner filament 140 and outer filament 130 may be formed from similar materials or different materials. Because inner filament 140 is being pulled and therefore incurring most of the force generated from the pulling, certain applications may be well suited with an inner filament 140 formed from a material possessing a higher tensile strength compared to that of the outer filament 130. The outer filament 130 may be formed from a lower tensile strength material as the outer filament 130 is being pulled from multiple points by the inner filament 130.

Other weave patterns are contemplated in addition to the pattern described above and shown in FIGS. 1-4. As an example, although FIG. 1 shows that the outer filament 130 is interwoven in and out of each of the crowns 121, outer filament 130 may also be interwoven in and out of every second crown 121. Generally speaking, the less number of crowns 121 the outer filament 130 is interwoven therethrough, the smaller the amount of collapse of the crowns 121 radially inwards. A smaller collapse of the crowns 121 may correspond to a smaller reduction in diameter of the end portion 150 of the stent 120. Such a configuration may be suitable in certain applications where maximum collapse of the crowns 121 is not needed. Furthermore, in yet another design variation, inner filament 140 may not be woven through each of the inner loops 131 of the outer filament 130. As an example, the inner filament 140 could be weaved through every other inner loop 140. Such a configuration of inner filament 140 with the outer filament 130 limits the extent to which the crowns 121 would collapse. Generally speaking, if the number of inner loops 131 through which the inner filament 140 extends therethrough is reduced by about half (as would be the case when the inner loop 131 is woven through every second inner loop 131), then the crowns 121 may only collapse to an extent that is approximately half as much as when the inner filament 140 is interwoven through every inner loop 131, assuming that all other design factors remain equal. The exact number of crowns 121 through which the outer filament 130 interweaves and the exact number of inner loops 131 through which the inner filament 140 interweaves and extends therethrough may depend, at least in part, on the extent to which the crowns 121 are required to collapse for a particular application.

The exact required length for the outer filament 130 may vary depending on its respective interweaving pattern. By way of example, if the outer filament 130 interweaves through all the crowns 121, then the outer filament 140 may be longer than a circumference of the end 110 of stent 120 when fully expanded so as to not constrain the end 110 of the expanded stent 120. The length of the inner filament 140 may depend, in part, on the number of inner loops 131 that inner filament 140 extends there through and the separation distance between the end 110 and the knot (located beyond the end 110). The length of the inner filament 140 may be less than that of the outer filament 130 but preferably is sufficiently long enough to possess adequate slack for accessing the region of the inner filament 140 beyond end 110 (e.g., the knot) for grasping and pulling thereat.

The above described collapsing structure 100 may comprise more than two filaments. For example, a third filament may be incorporated into the two-filament collapsing structure 100. Referring to FIG. 3, the third filament (not shown) could be interwoven through the loops of the inner filament 140. The third filament would become the innermost filament of the three-filament collapsing structure. The third filament would be pulled along a free end extending beyond the end 110 of stent 120. The effect would be a reduction in the collapse of the crowns 121 as compared to the two-filament collapsing structure 100. The exact number of filaments to use in a particular collapsing structure would depend, at least in part, on the degree of collapse of the crowns 121 required for a particular procedure.

Although all the embodiments have shown a self-expandable braided stent structure, the collapsing structure 100 may also be incorporated onto other stent structures, such as, for example, a z-stent having zigzag struts. If the contemplated stent structure is a z-stent, the outer filament 130 could be extended through the eyelets at one of the ends of the z-stent. The inner filament 140 could subsequently be interwoven through loops created by the outer filament 130 extending through eyelets.

The collapsing structure 100 can be utilized in a number of different applications. For example, the collapsing structure 100 can be affixed to an end of the stent 120 to enable grasping of the inner filament 140 with a retrieval member for removal from a body lumen or repositioning within the body lumen.

Figure 5:
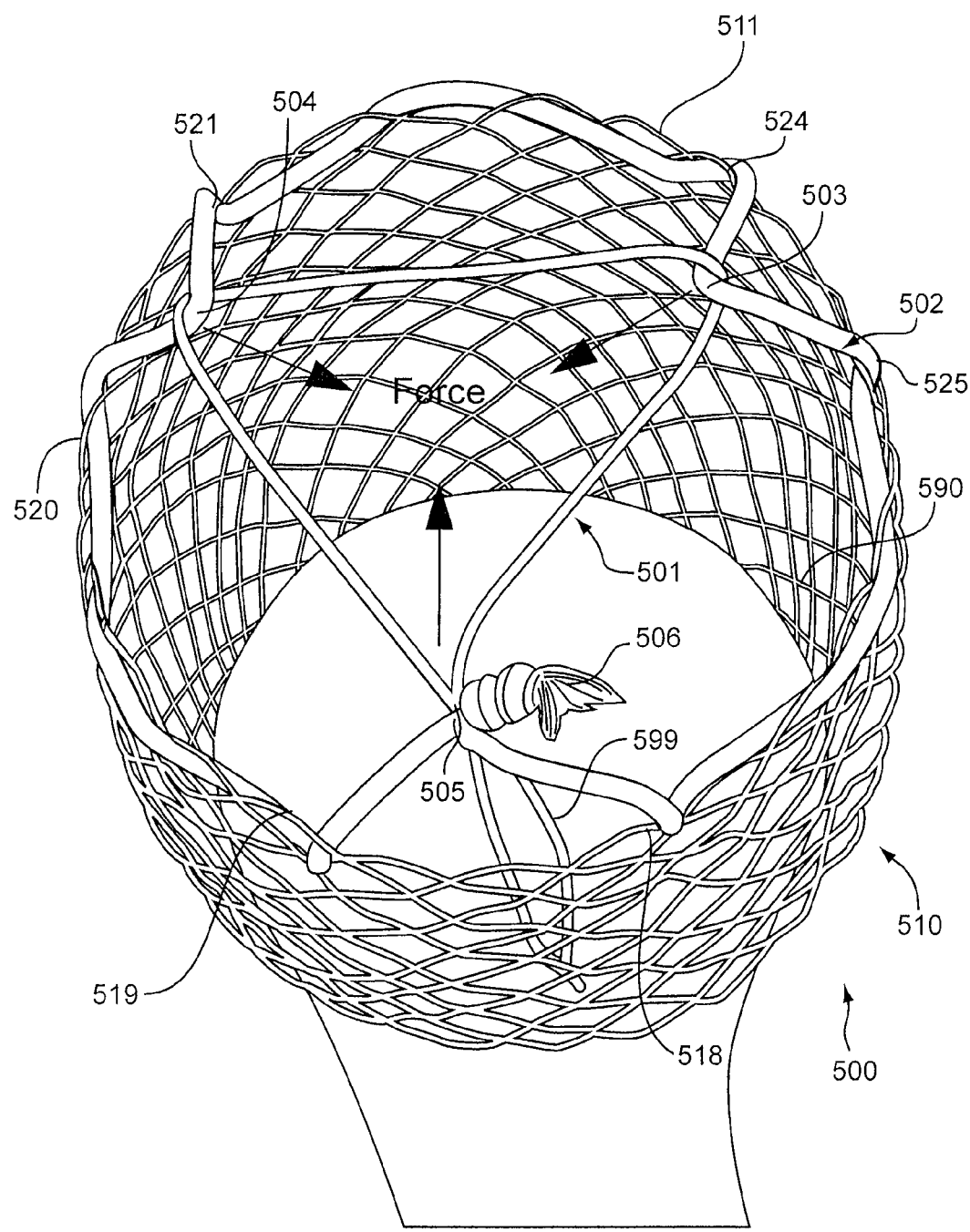
FIG. 5 shows an inner filament engaged with an outer lasso at three locations along a proximal end of a stent.

Other applications for an inner filament engaged with an outer filament are contemplated in addition to the repositioning and the removal of a deployed stent, as has been described above. For example, FIG. 5 shows a collapsing structure 500 comprising an inner filament 501 engaged to an outer filament or lasso 502 at a proximal end 510 of a stent 511, which is shown in its expanded state. The collapsing structure 500 may control the positioning of the outer lasso 502 during loading of the stent 511 into a delivery system (not shown). FIG. 5 shows that the inner filament 501 is wrapped around three inner loops 503, 504 and 505 of the outer lasso 502.

Figure 6:
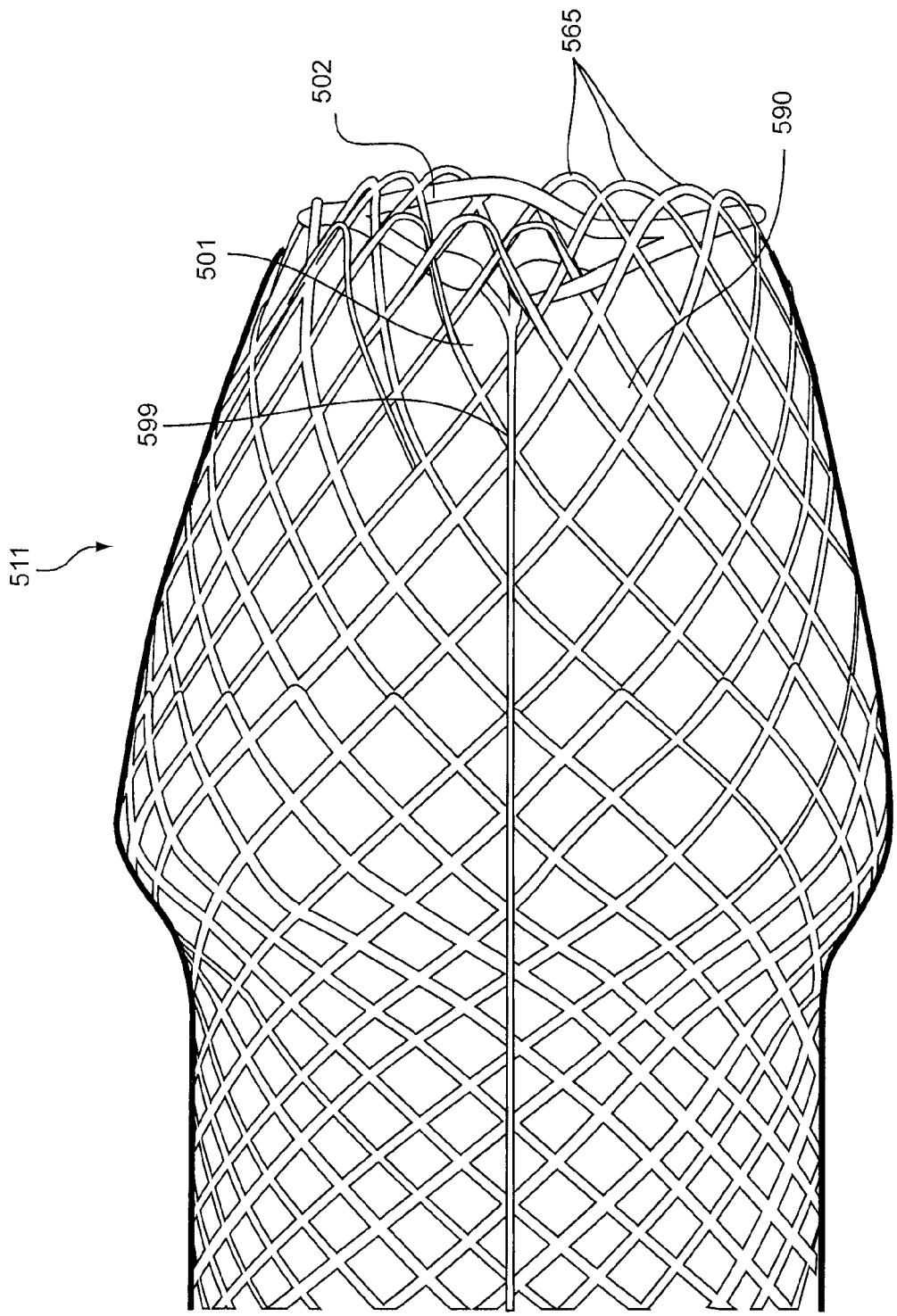
FIG. 6 shows the stent of FIG. 5 with a portion of the inner filament being pulled in a distal direction so as to draw the outer lasso into the stent lumen.

During stent 511 loading into a delivery system, the inner filament 501 may be pulled along portion 599 of the inner filament 501 in a distal direction as shown in FIG. 6. Portion 599 extends from the proximal end 510 to a distal end of the stent 511, as shown in FIG. 6. The pulling force is transmitted to the inner loops 503, 504, and 505 (as shown by the three arrows in FIG. 5) to cause the outer lasso 502 to move into the lumen 590 of the stent 511 (FIG. 6). When the stent 511 is compressed during the loading procedure and the outer lasso 502 has been moved into the lumen of the stent 511 (FIG. 6), an outer sheath (not shown) can be slidably disposed over the stent 511 to constrain the stent 511 for subsequent delivery and deployment. The ability to selectively move the outer lasso 502 into the lumen 590 protects the lasso 502 from becoming potentially damaged during advancement of the outer sheath over the stent 511 or during the loading of the stent 502 into the delivery system (e.g., by advancing the stent 511 through a funnel component). After the outer sheath is slidably disposed over the stent 511, the inner filament 501 may be cut and removed from the stent 511 and from the delivery system. The outer lasso 502 remains woven to the proximal end 510 of the stent and serves as the means for repositioning and/or removing the stent 511 after deployment.

FIG. 5 shows that the inner loops 503, 504, and 505 are created by interweaving the outer lasso 502 through crowns of the stent 511. A first inner loop 503 is created as outer lasso 502 moves into opening of crown 524 and into opening of crown 525. A second inner loop 504 is created as outer lasso 502 moves into opening of crown 520 and into opening of crown 521. A third inner loop 505 is created as outer lasso 502 moves into opening of crown 519 and into opening of crown 518. The size of each of the loops 503, 504, and 505 is determined at least in part by the spacing between the two crowns forming each of the loops. In this example, FIG. 5 shows that the distance between adjacent crowns forming each loop 503, 504, and 505 is about two crowns.

The engagement of the inner filament 501 with the outer lasso 502 at three locations enables the outer lasso 502 to collapse within the lumen 590 of the stent 511 (FIG. 6). FIG. 6 shows that pulling portion 599 in a distal direction causes the inner loops 503, 504, and 505 to also be pulled distally into the lumen 590. The inner loops 503, 504, and 505 transmit the pulling force from the inner filament 130 to the outer lasso 502. In other words, the inner loops 503, 504, and 505 pull on the outer lasso 502, thereby causing the outer lasso 502 to tighten and be drawn distally inwards towards the lumen 590 of the stent 511. The pulling of the outer lasso 502 into the lumen 590 causes the crowns 565 to collapse radially inwards a predetermined amount, as shown in FIG. 6.

Engagement of the inner filament 501 with the outer lasso 502 at the three locations where the inner loops 503, 504, and 505 are located allows the outer lasso 502 to be drawn into the lumen 590. The outer lasso 502 need not be woven through all the crowns 565 to achieve such a collapse of the outer lasso 502 within the lumen 590. Because the outer lasso 502 may not be required to be woven through every crown 565 along the proximal end 510 of the stent 500, the outer lasso 502 does not generate as much frictional resistance to the stent 500 as an outer lasso 502 that is woven through all the crowns 565. Accordingly, the application of the force along portion 599 of the inner filament 501 may be less than the force required to pull or draw an outer lasso 700 as configured in FIG. 7. In contrast to a two filament system, the single outer lasso 700 shown in FIG. 7 needs to be woven through at least every other crown to allow the lasso 700 to adequately collapse within the stent lumen. Such a configuration may create a significantly higher force requirement to collapse the outer lasso 700 within the stent lumen because of the higher frictional resistance created as the lasso 700 is pulled through the crowns about the end of the stent. The lower frictional resistance of the outer lasso 502 with the proximal end 510 of the stent 511 in the configuration shown in FIGS. 5 and 6 allows the stent 511 to radially expand upon either deployment or release of tension from the inner filament 501 during a repositioning procedure of the stent 511.

FIG. 5 shows that the free ends of the outer lasso may be tied to form a knot 506. The absence of a portion of the outer lasso 502 extending beyond the proximal end 510 of the stent 511 (as compared to the lasso 700 in FIG. 7 which has a grasping portion 701) may reduce the likelihood of the lasso loop 502 being inadvertently damaged during loading of the stent 511 into the delivery system. Additionally, a shorter length of the outer lasso 502 extending beyond the proximal end 510 of the stent 511 may reduce the likelihood that the lasso 502 inadvertently is pinched between the body of the stent 511 and the body lumen or ends up at another unintended location within the delivery system that is difficult to access when the stent 511 is ready to be released therefrom and deployed.

It should be understood that the configuration of FIG. 5 can be used on a variety of stent architectures that are either self-expandable or balloon-expandable. Other structures in addition to that of FIG. 5 are contemplated to engage an outer lasso and thereafter draw it into the stent lumen during a loading or re-sheathing procedure. For example, engagement between an inner filament and outer lasso at more than three locations is possible. Greater than three locations or points of engagement between the inner filament and the outer lasso may further reduce the amount of resistance the stent has to overcome to radially expand to its expanded state.

The above figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims. Furthermore, the advantages described above are not necessarily the only advantages of the invention, and it is not necessarily expected that all of the described advantages will be achieved with every embodiment of the invention.

The invention claimed is:

1. A collapsing element for removing or repositioning a stent, comprising:
    a first filament interwoven through a plurality of crowns extending about a stent end, wherein the interweaving of the first filament through the plurality of crowns creates a plurality of loops disposed about the stent end;
    a second filament interwoven through at least a portion of the plurality of the loops of the first filament, the second filament configured to be pulled so as to pull the loops of the first filament radially inwards and thereby pull the plurality of crowns towards each other to collapse the stent end;
    a closed grasping loop operably connected to the second filament, the grasping loop being biased in an open configuration and configured to be grasped by an elongate medical instrument; and
    a tube covering the grasping loop, the grasping loop extending through a lumen of the tube, the tube being configured to bias the grasping loop in an open configuration, the tube further being configured to remain attached to the grasping loop following deployment of the stent,
    wherein the second filament and the grasping loop are each configured to remain operably connected to the stent following deployment.

2. The collapsing element of claim 1, wherein the plurality of loops comprises a first plurality of inner loops that alternates with a second plurality of outer loops.

3. The collapsing element of claim 2, wherein each of the first plurality of inner loops are disposed within a lumen of the stent and created by the first filament extending into an interior opening of a corresponding first crown within the stent lumen and thereafter passing out from the stent lumen through an interior opening of a corresponding second crown.

4. The collapsing element of claim 3, wherein each of the second plurality of the outer loops are disposed outside from the stent end and created by the first filament emerging out of the stent from the corresponding second crown and thereafter passing into the stent lumen through an interior opening of a corresponding third crown.

5. The collapsing element of claim 2, wherein each of the second plurality of the outer loops of the first filament exerts a radially inward force against adjacent crowns to reduce a diameter of the stent end.

6. The collapsing element of claim 1, wherein the plurality of crowns substantially reside in a single plane traverse to a longitudinal axis of the stent, and further wherein the plurality of crowns each comprise an apex that extends longitudinally outwardly from the stent end.

7. The collapsing element of claim 6, wherein a spacing between adjacent crowns decreases when each of the adjacent crowns collapses.

8. The collapsing element of claim 1, wherein a distance as measured from an apex of each of the first plurality of inner loops to each of the plurality of crowns increases as the stent end collapses from an expanded state, and further wherein a distance from an apex of each of the second plurality of outer loops to each of the plurality of crowns decreases as the stent end collapses from the expanded state.

9. The collapsing element of claim 1, wherein the second filament is interwoven substantially perpendicular to the inner loops of the first filament.

10. The collapsing element of claim 1, wherein the first filament comprises a length longer than a circumference of the stent end in an expanded state, the length being sufficient to allow the stent end to substantially fully expand to the expanded state.

11. The collapsing element of claim 1, wherein the first filament is interwoven through each of the plurality of the crowns extending about the stent end.

12. The collapsing element of claim 1, wherein the first filament is interwoven through alternating crowns of the plurality of crowns.

13. The collapsing element of claim 1, wherein the first filament passes through at least three of the plurality of crowns.

14. The collapsing element of claim 1, wherein the second filament passes through at least three of the loops of the first filament.

15. The collapsing element of claim 1, wherein the second filament further comprises a first free end and a second free end tied together to form a closed loop that is separate from the grasping loop.

16. The collapsing element of claim 1, wherein the second filament further comprises a first free end and a second free end tied together to form a knot, and the grasping loop is affixed to the knot.

17. The collapsing element of claim 16 where the knot is an overhand knot.

18. The collapsing element of claim 1 further comprising a coiled radiopaque wire disposed about at least a portion of the grasping loop and within the tube covering the grasping loop and configured to remain attached to the grasping loop following deployment of the stent, the coiled radiopaque wire and tube being configured to be grasped by the elongate medical instrument.

19. A collapsing element for removing or repositioning a stent, comprising:
    a first filament interwoven through a plurality of crowns extending about a stent end, wherein the interweaving of the first filament through the plurality of crowns creates a plurality of loops disposed about the stent end;
    a second filament interwoven through at least a portion of the plurality of the loops of the first filament, the second filament configured to be pulled so as to pull the loops of the first filament radially inwards and thereby pull the plurality of crowns towards each other to collapse the stent end; and
    a closed grasping loop operably connected to the second filament, the grasping loop being biased in an open configuration and configured to be grasped by an elongate medical instrument,
    wherein the second filament further comprises a first free end and a second free end tied together to form a first knot and a second knot spaced apart from the first knot, the first knot and the second knot defining the grasping loop there between, wherein a first portion of the first free end extending between the first knot and the second knot is longer than the second portion of the second free end extending between the first knot and the second knot so as to form an asymmetric grasping loop, and
    wherein the second filament and the grasping loop are each configured to remain operably connected to the stent following deployment.

20. A collapsing structure for removing or repositioning a stent deployed within a bodily lumen, comprising:
    an outer filament interwoven through a plurality of crowns about a stent end to create an alternating arrangement of a plurality of inner loops and a plurality of outer loops, the plurality of inner loops disposed within a lumen of the stent and the plurality of outer loops disposed outside from the stent end;
    an inner filament interwoven through each of the plurality of the inner loops to create a plurality of engagement points for pulling the outer filament, wherein pulling the outer filament at each of the plurality of engagement points draws the plurality of crowns inwardly toward a central longitudinal axis of the stent; and
    a grasping loop operably connected to the inner filament, wherein pulling the grasping loop pulls the inner filament so as to draw the plurality of crowns inwardly toward the central longitudinal axis of the stent, the grasping being configured to be grasped by an elongate medical instrument; and
    a radiopaque tubular member disposed over and non-removably connected to the grasping loop, the radiopaque tubular member being configured to bias the grasping loop in an open configuration, the radiopaque tubular member being further being configured to be grasped by the elongate medical instrument,
    wherein the outer filament, the inner filament and the grasping loop each comprise a non-expandable closed loop, and
    wherein the outer filament, the inner filament, the grasping loop and the radiopaque tubular member are each configured to remain operably connected to the stent following deployment.

21. The structure of claim 20, wherein the number of inner loops is at least three.

22. The structure of claim 20, wherein a first free end and a second free end of the outer filament are tied together at a plurality of spaced apart locations to form the grasping loop.

23. The structure of claim 20, wherein each of the grasping loop, the outer filament and the inner filament is formed from suture material.

24. The structure of claim 20, wherein the inner filament is configured to engage with the outer filament at the plurality of engagement points to draw in the outer filament within the lumen of the stent.

* * * * *